United States Patent
Elliott

(10) Patent No.: US 7,793,662 B2
(45) Date of Patent: Sep. 14, 2010

(54) EARPLUG

(76) Inventor: James Carson Elliott, 5708 179th Ave. SE., Bellevue, WA (US) 98006

( * ) Notice: Subject to any disclaimer, the term of this patent is extended or adjusted under 35 U.S.C. 154(b) by 0 days.

(21) Appl. No.: 11/353,878

(22) Filed: Feb. 14, 2006

(65) Prior Publication Data

US 2006/0180387 A1    Aug. 17, 2006

Related U.S. Application Data

(60) Provisional application No. 60/653,043, filed on Feb. 14, 2005.

(51) Int. Cl.
*A61F 11/00* (2006.01)
(52) U.S. Cl. ...................... 128/864; 181/135
(58) Field of Classification Search ................. 128/864, 128/866, 867; 181/129, 130, 135
See application file for complete search history.

(56) References Cited

U.S. PATENT DOCUMENTS

| | | | | |
|---|---|---|---|---|
| 4,372,904 A * | 2/1983 | Gunn | .......................... | 264/134 |
| 4,434,794 A * | 3/1984 | Leight | .......................... | 128/867 |
| 5,920,636 A * | 7/1999 | Oliveira et al. | .............. | 381/328 |
| 5,957,136 A * | 9/1999 | Magidson et al. | ........... | 128/864 |
| 5,996,584 A * | 12/1999 | Oliveira et al. | .............. | 128/864 |
| 6,006,857 A * | 12/1999 | Leight et al. | ................. | 181/135 |
| 6,484,726 B1 * | 11/2002 | Remer et al. | ................. | 128/864 |
| 6,820,717 B2 * | 11/2004 | Fleming et al. | ............. | 181/135 |
| 6,904,773 B1 * | 6/2005 | Cushman | ....................... | 66/1 A |
| 7,096,872 B2 * | 8/2006 | Ligon et al. | ................. | 128/864 |

* cited by examiner

*Primary Examiner*—Patricia M Bianco
*Assistant Examiner*—Camtu T Nguyen
(74) *Attorney, Agent, or Firm*—Christensen O'Connor Johnson Kindness PLLC

(57) ABSTRACT

An earplug (100) having an adjustable sound deadening rating is disclosed. The earplug (100) includes an ear piece (102) adapted to fit within a user's ear canal and a core (104). The core (104) has a predetermined sound deadening rating. The ear piece (102) includes a coupling assembly (106) for removably coupling the core (104) to the ear piece (102) such that the core (104) may be removed from the ear piece (102) and replaced with another core (108) having a different preselected sound deadening rating to adjust a sound deadening rating of the earplug.

5 Claims, 1 Drawing Sheet

EARPLUG

CROSS-REFERENCE TO RELATED APPLICATION

This application claims the benefit of U.S. Provisional Application No. 60/653,043, filed Feb. 14, 2005, priority from the filing date of which is hereby claimed under 35 U.S.C. §119(e).

BACKGROUND

In previously developed earplugs, a sound deadening capability of the earplug is not adjustable to varying sound deadening needs. For instance, in certain situations, a user may desire less sound deadening from an earplug, such that they may better hear certain sounds, such as sounds indicating approaching danger or conversation. In other instances, the user may desire more sound deadening from an earplug to better protect the ear or provide a more quite environment. In previously developed earplugs, the earplugs are not adjustable to meet varying sound deadening needs. Therefore, a user of previously developed earplugs was required to buy, and keep on hand, a plurality of pairs of earplugs such that the user could switch out a pair of earplugs with another pair of earplugs having a different sound deadening ability.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

One embodiment of an earplug formed in accordance with one embodiment of the present invention and having an adjustable sound deadening rating is disclosed. The earplug includes an ear piece adapted to fit within a user's ear canal and a core. The core has a predetermined sound deadening rating. The ear piece includes a coupling assembly for removably coupling the core to the ear piece such that the core may be removed from the ear piece and replaced with another core having a different preselected sound deadening rating to adjust a sound deadening rating of the earplug.

One embodiment of an earplug kit formed in accordance with the present invention is also disclosed. The earplug kit includes at least one ear piece adapted to fit within a user's ear canal. The earplug kit also includes at least a first core and a second core. The first core has a first sound deadening rating and the second core has a second sound deadening rating that is higher or lower than the first sound deadening rating. The first and second cores are each adapted to be removably received by the ear piece to form an earplug such that the first core may be replaced by the second core to selectively adjust a sound deadening rating of the earplug.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While the preferred embodiment of the invention has been illustrated and described, it will be appreciated that various changes can be made therein without departing from the spirit and scope of the invention.

Figure 1:
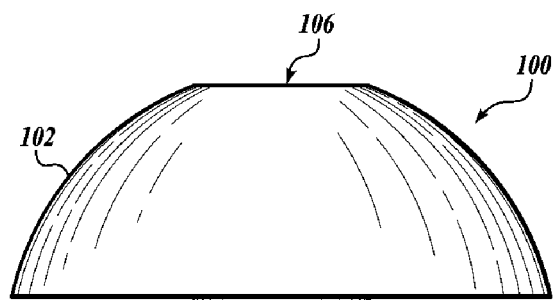
FIG. 1 is an elevation view of one embodiment of an earplug formed in accordance with the present invention.
Figure 2:
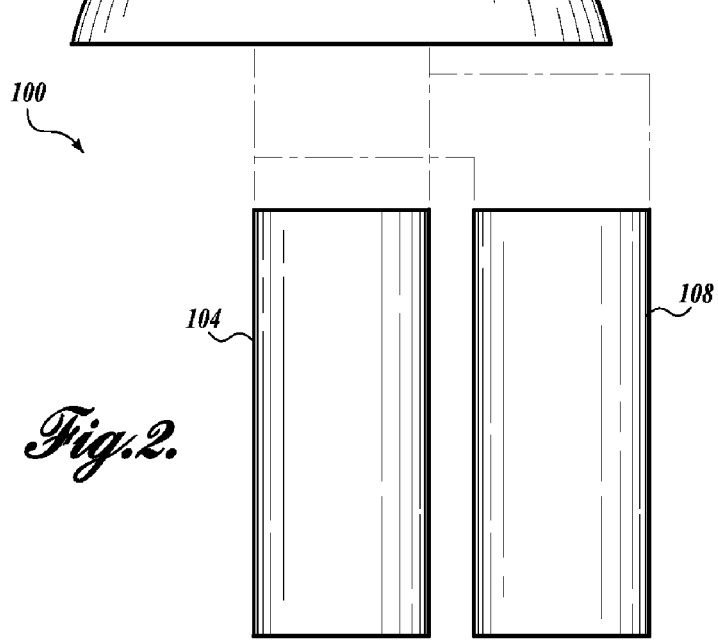
FIG. 2 is an elevation view of the earplug of FIG. 1 showing a core of the earplug being removed and replaced with an alternate core having a different sound deadening rating.
Figure 3:
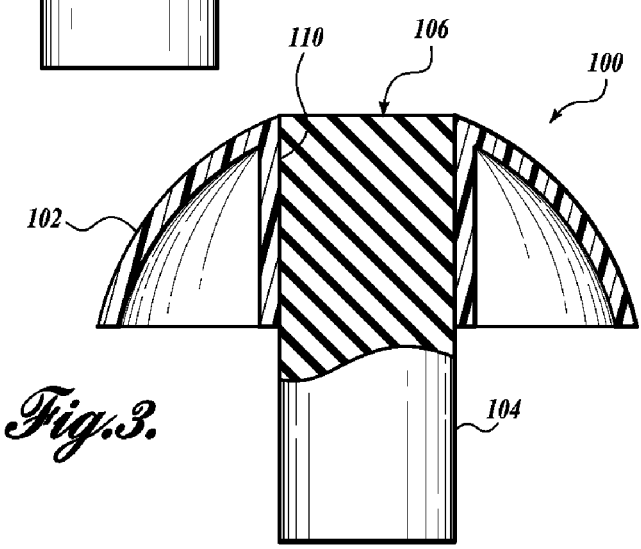
FIG. 3 is a cross-sectional view of the earplug of FIG. 1, the cross-sectional cut taken substantially along a centerline of the earplug.

One embodiment of an earplug 100 formed in accordance with the present invention is shown in FIGS. 1-3. Generally described, the earplug 100 includes an ear piece 102 adapted to fit within a user's ear canal and a core 104. The core 104 has a predetermined sound deadening rating. The ear piece 102 includes a coupling assembly 106 for removably coupling the core 104 to the ear piece 102 such that the core 104 may be removed from the ear piece 102 and replaced with another core 108 having a different preselected sound deadening rating to adjust a sound deadening rating of the earplug 100.

In light of the above general description of the earplug 100, this detailed description will now focus in greater detail upon the structure of the earplug 100. As stated above, the earplug 100 includes an ear piece 102. The ear piece 102 of the illustrated embodiment is a pliable diaphragm that is adapted to form a comfortable seal just inside the ear canal of the user and to hold the core 104 at least partially within the ear canal. The ear piece 102 of the illustrated embodiment is preferably tapered to better fit within the ear canal of the user. For instance, the ear piece 102 may be tapered to expand in diameter along the length of the ear piece 102, a few suitable examples being ear pieces that are conical in shape, frusto-conical in shape, dome-shaped (as shown in FIGS. 1-3), semi-spherical in shape, formed from ribs of increasing diameter, etc.

The ear piece 102 is preferably made from a pliable material, a few suitable examples being silicon, foam, rubber, etc. The ear piece 102 is preferably made from a material that is able to conform to the shape of the user's ear canal and provides, at least partially, a seal between the ear piece 102 and the ear canal to impede the passage of sound therethrough while holding the core 104 at least partially in the ear canal of the user. The ear piece 102 is also preferably formed from an elastic material able to bias the outer surface of the ear piece 102 outward to engage the ear canal with a preselected force to enhance the seal between the ear canal and the ear piece 102. One suitable example of an ear piece 102 suitable for use with the present invention is the ear piece used with SONY'S FONTOPIA HEADPHONES, product number MDR-EX51LP, although it should be apparent that the ear piece 102 may be designed in accordance with any currently available ear piece design hereto known or to be developed.

The ear piece 102 includes the coupling assembly 106. The coupling assembly 106 of the illustrated embodiment includes an aperture, bore, or sleeve 110 in the ear piece 102. The diameter of the sleeve 110 is selected such that the core 104 is received within the sleeve 110 in an interference fit arrangement. Moreover, the sleeve 110 is elastic such that upon insertion of the core 104 within the sleeve 110, the sleeve 110 squeezes the core 104 to removably hold the core 104 at least partially within the ear piece 102. In the illustrated embodiment, the coupling assembly 106 is illustrated and described as comprising a sleeve 110 receiving the core 104 in an interference fit arrangement, however, it should be apparent to those skilled in the art that the coupling assembly 106 may be formed in any suitable manner permitting the removable coupling of the ear piece 102 to the core 104, a few suitable examples being a bayonet type coupling assembly, a quick connect type coupling assembly, a snap fit coupling assembly, etc.

The core 104 of the illustrated embodiment is cylindrical in shape, although it should be apparent to those skilled in the art that the core 104 may be alternately shaped in any shape having a volume without departing from the spirit and scope of the present invention. The core 104 of the illustrated embodiment is preferably selected to have a diameter that may be removably received by the sleeve 110 of the ear piece 102 in an interference fit arrangement as described above.

The core 104 may be made from any rigid, semi-rigid, or pliable material able to deaden sound. A few suitable examples of suitable materials are foam, gel, silicone, plastic, organic or inorganic fibrous materials, etc. The core 104 is manufactured to provide the earplug 100 with a preselected sound deadening rating, such as a sound deadening rating falling between 1 and 40 decibels. Preferably, different cores 104 and 108 are manufactured with different materials, densities, shapes, passageways through the core, and/or voids to provide cores 104 and 108 with differing sound deadening capabilities. Providing cores 104 or 108 with differing sound deadening capabilities permits the core 104 of the earplug 100 to be selectively removed and replaced with an alternate core 108 to selectively adjust the sound deadening rating of the earplug 100, as the user's need for sound deadening changes.

Cores of differing sound deadening capabilities are preferably indicated by indicia designating their sound deadening capabilities. The indicia may be visual in nature, such as color or text designations indicating the sound deadening capabilities of the cores, or may be physical in nature, such as the shape of the core or raised or sunken text or bumps disposed on the core, etc., indicating the sound deadening capabilities of the cores.

It will be further appreciated by those skilled in the art and other that a first cores and a second core, such as cores 104 and 108, can be provided along with the earpiece 102 to provide an earplug kit in accordance with an embodiment of the present invention.

In light of the above description of the structure of the earplug 100, the operation of the earplug 100 will now be described. Referring to FIG. 1, a user inserts the earplug 100 within the ear canal, inserting the small end of the tapered ear piece 102 first into the ear canal. The ear piece 102 at least partially seals against the ear canal, and with the aid of the core 104, reduces sound levels for the user by a specific decibel rating, such as 15 dB. This low level of sound reduction permits the user to still be aware of sounds present in the user's environment, but at a reduced level to aid in helping reduce hearing loss.

Turning to FIG. 2, upon entering a louder environment or upon desiring a higher level of hearing protection in the same environment, the user may remove the earplug 100 and replace the core 104 with another core 108 having a higher sound deadening capability. Upon reinserting the earplug 100 within the ear canal, the user enjoys a higher level of sound deadening, such as 25 dB. Alternatively, as will be appreciated by those skilled in the art and others, the user may simply remove the core 104 and couple another core 108 with the ear piece 102 positioned in the user's ear canal.

As should further be apparent to those skilled in the art, the earplug 100, and the components forming the earplug 100, such as the ear piece 102 and the cores 104 and/or 108, may be offered as a one size fits all solution or may be offered in varying sizes to meet the needs of various users, such as small, medium, and large.

Of note, for the purposes of this detailed description, references to decibels refers to decibels determined by standard attenuation hearing tests well known to those skilled in the art.

The embodiments of the invention in which an exclusive property or privilege is claimed are defined as follows:

1. An earplug kit comprising:
   an ear piece having first and second ends and an open bore extending through the ear piece between the first and second ends;
   a first core having first and second ends, a length greater than the distance between the ear piece first and second ends, and a first sound deadening rate; and
   a second core having first and second ends, a length greater than the distance between the ear piece first and second ends, and a second sound deadening rate different from the first sound deadening rate;
   wherein the first and second cores are each removably coupleable with the ear piece by inserting the first or second core exclusively into the open bore, and wherein the first end of the first or second core when removably coupled with the ear piece is substantially flush with the first end of the ear piece.

2. An earplug kit comprising:
   an ear piece adapted to fit in a user's ear canal, the ear piece having first and second ends and an open bore extending through the ear piece from the first end to the second end;
   a first core having first and second ends and a first sound deadening rating; and
   a second core having first and second ends and a second sound deadening rating higher or lower than said first sound deadening rating,
   wherein said ear piece includes a coupling assembly and said first and second cores are each adapted to be fitted within the open bore of the ear piece;
   wherein fitting one of said first and second cores into the open bore of said ear piece creates an assembled earplug, the assembled earplug having an assembled sound deadening rating; and
   wherein the user's removing of said first core and replacing it with said second core in the open bore changes the sound deadening rating of the assembled earplug.

3. An earplug kit comprising:
   an earplug body having a proximal end and a distal end and an open bore extending through the body from the proximal and to the distal end; and
   two or more cores made of materials having different sound deadening capabilities, wherein each of the two or more cores is insertable into the open bore to change the sound deadening capability of the earplug.

4. The earplug of claim 3, wherein the two or more cores have different colors to indicate a different sound deadening capability.

5. The earplug of claim 3, wherein the two or more cores have markings to indicate a different sound deadening capability.

* * * * *

UNITED STATES PATENT AND TRADEMARK OFFICE
CERTIFICATE OF CORRECTION

| | | | |
|---|---|---|---|
| PATENT NO. | : 7,793,662 B2 | | Page 1 of 1 |
| APPLICATION NO. | : 11/353878 | | |
| DATED | : September 14, 2010 | | |
| INVENTOR(S) | : J. C. Elliott | | |

It is certified that error appears in the above-identified patent and that said Letters Patent is hereby corrected as shown below:

| COLUMN | LINE | ERROR |
|---|---|---|
| 2 (Claim 3, | 52 line 4) | "and to the distal end; and" should read --end to the distal end; and-- |

Signed and Sealed this
Fifteenth Day of March, 2011

David J. Kappos
*Director of the United States Patent and Trademark Office*